United States Patent

Roth

Patent Number: 5,840,053
Date of Patent: Nov. 24, 1998

[54] DEVICE FOR FOOT STABILIZATION

[75] Inventor: Ivar E. Roth, Corona del Mar, Calif.

[73] Assignee: American Arch LLC, Newport Beach, Calif.

[21] Appl. No.: 539,426

[22] Filed: Oct. 5, 1995

Related U.S. Application Data

[63] Continuation of Ser. No. 324,257, Oct. 17, 1994, abandoned.

[51] Int. Cl.⁶ ........................................................ A61F 5/30
[52] U.S. Cl. ............................................... 602/66; 36/145
[58] Field of Search ................................ 602/66; 36/145, 36/154, 161, 166, 170, 178, 180

[56] References Cited

U.S. PATENT DOCUMENTS

| | | | |
|---|---|---|---|
| 822,138 | 5/1906 | Little | 602/66 |
| 987,599 | 3/1911 | Quenzer | 602/66 |
| 1,267,796 | 5/1918 | Pakas | 36/166 |
| 1,492,514 | 4/1924 | Jensen | 602/66 |
| 1,538,026 | 5/1925 | Cramer | 602/66 |
| 1,651,285 | 11/1927 | Levick, Jr. | 602/66 |
| 1,901,659 | 3/1933 | Larack | 36/145 X |
| 2,358,966 | 9/1944 | Einstoss | 602/66 |
| 4,271,605 | 6/1981 | Raczka | 36/28 |

FOREIGN PATENT DOCUMENTS 485313  5/1938  United Kingdom ..................... 602/66

*Primary Examiner*—Richard J. Apley
*Assistant Examiner*—Kim M. Lee
*Attorney, Agent, or Firm*—McDermott, Will & Emery

[57] ABSTRACT

A supportive device for the longitudinal arch of the foot is comprised of a fabric-coated elasticized strap enclosing a specially designed pad of rubberized material. This strap is wrapped snugly around the longitudinal arch with the enclosed pad strategically placed to provide optimum arch support and secured by a VELCRO-type fastener strip.

9 Claims, 3 Drawing Sheets

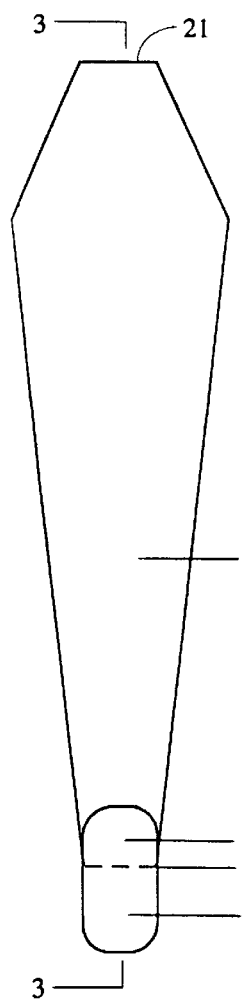
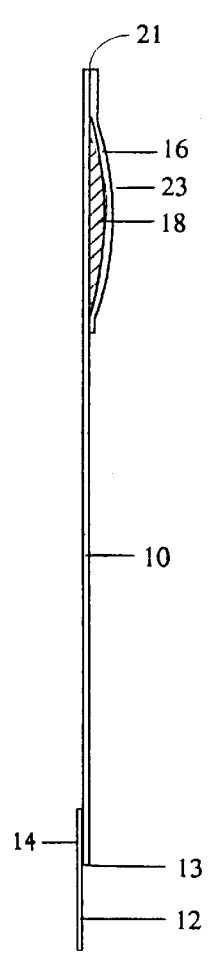
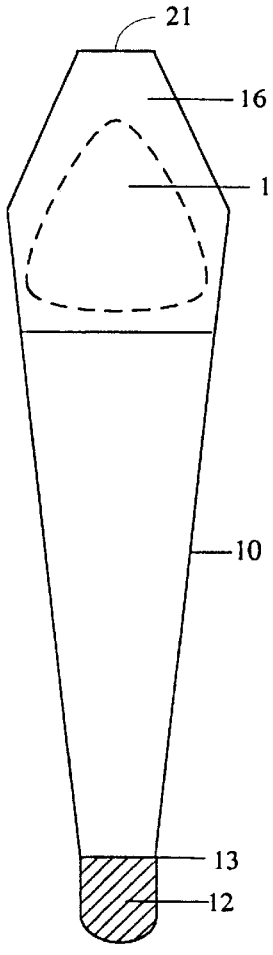
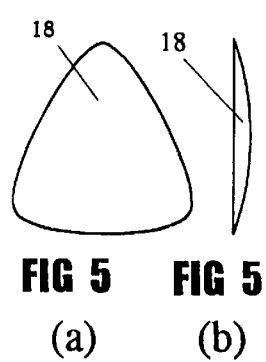
FIG 2     FIG 3     FIG 4     FIG 5 (a)     FIG 5 (b)

DEVICE FOR FOOT STABILIZATION

This is a continuation of application Ser. No. 08/324,257 filed on Oct. 17, 1994, now abandoned.

BACKGROUND OF THE INVENTION

1. Field of the Invention

The invention relates generally to orthopedic devices for the foot and more specifically to supporting the longitudinal arch of the foot in a simple, unobtrusive manner.

2. Description of the Prior Art

There are two anatomical arches of the foot, the transverse (metatarsal) arch and the longitudinal arch. The invention is concerned only with the longitudinal arch. Supporting this arch by mechanical means is an indicated and accepted modality for several conditions of the foot. General foot fatigue/excessive pronation and heel spur syndrome/plantar fasciitis are two of the more common conditions.

Pronation of the foot, although technically a motion involving all three anatomic planes, is essentially a rolling in of the foot and ankle, or in even more simple terms, a collapsing of the longitudinal arch. Pronation along with its opposite counterpart, supination, is a regular and essential part of foot function when it occurs within a "normal" range. When excessive pronation occurs, however, problems usually result. To begin with, motion in joints that are not supposed to have much motion (hypermobility) cause muscles which are not used to working during certain phases of gait or stance to become active in order to stabilize these joints. The most immediate result of this increased muscular demand is foot and leg fatigue. Over a period of time additional pathology may result from this pronation syndrome.

One of these additional effects is on the plantar fascia, a thick ligamentous band along the plantar (bottom) surface of the foot which inserts into the heel. It is generally agreed that pronation increases the tension or pull on this ligament away from its attachment to the heel resulting in a painful inflammation known as plantar fasciitis. If unchecked over time this process may progress to the formation of a bone spur on the heel. This combination of plantar fasciitis and heel spur is usually referred to as heel spur syndrome. Any device that can resist, limit, or stabilize this pronation tendency to any degree will allow its wearer to stand or walk in greater comfort and reduce the chances of further pathology. At present, the most widely accepted, effective and long term method of providing this support is by means of molded arch support devices, commonly called arch supports or orthotic devices. These devices are made from a wide range of materials and may be customized by a physician at the high monetary end of the spectrum or purchased as an over-the-counter commercial item from many outlets at the low end. They are durable and provide consistent results over time.

Their major disadvantages, besides cost, are: (1) the space they take up in shoes, particularly in persons with high-arched feet; (2) not all types of shoes accommodate them (open types do not); and (3) their impracticality for certain athletes that require little or no footwear, such as dancers or gymnasts.

Strapping the foot or ankle with various types of adhesive tape to maintain optimal function has also been a mainstay method of addressing the problem of support. While this method is quite practical for short term use by physicians and professional trainers, it has numerous drawbacks. For example: (1) For optimal results it should be applied by a professional, which rules out self-application. (2) It stretches and loses its effectiveness quickly (two or three days is usually the maximum limit for wear). (3) It can be used only once. (4) No adjustment is possible after the initial application. Finally, (5) adhesive material may be irritating to the skin, can facilitate fungal infections, and has the potential for allergic reactions.

Other non-orthotic devices which support the longitudinal arch in varying ways: THE RESUPINATOR (U.S. Pat. Nos. 4,392,487 and 4,753,228) is a device designed to "effectively control the alignment of the foot". It includes one elastic component of a relatively inelastic material which slips over the forefoot and another component, a long adjustable strap, which is wrapped around the heel and secured by a VELCRO fastener. As the name implies, its goal is to resupinate the foot, an action opposite to pronation. Although the theory seems plausible, several disadvantages are readily apparent. For example: (1) It appears somewhat complicated to put on. (2) It comes in five sizes with both right and left models. (3) Because it covers a relatively large area of the foot this device could be irritating to the skin and (4) its bulk could make wearing in most shoes uncomfortable and/or impossible. (5) The number of stitched seams in this device would increase its manufacturing cost and (6) become another factor for potential skin irritation.

COUNT-R-FORCE (U.S. Pat. No. 3,926,186) is a device "designed to fit your foot and support the ligaments, tendons and muscles". It consists of a large, stitched, nylon-covered cushion which is placed under the longitudinal arch and secured by two (2) VELCRO fastener strips. Its major advantage is in sizing, there is no right or left and one size fits all. Its disadvantages are: (1) it is rather bulky which could affect shoe fit; (2) the VELCRO straps come directly in contact with the skin which could cause irritation; (3) because of its nylon construction there may be some migration or slippage during wear; (4) it contains a foam padding material which only resists bottoming out; (5) the number of stitched seams in this device would increase its manufacturing cost and (6) be another factor for potential skin irritation.

Although not an arch support device, the Metatarsal Arch Cushion Support (U.S. Pat. No. 3,086,520) will be briefly mentioned here only because it incorporates a pad of somewhat comparable design within an encircling, elasticized band. However, there are three major differences in concept between this device and the present device. (1) The pad is oriented perpendicular to its encircling band instead of parallel and (2) it is designed solely to support the metatarsal arch, not the longitudinal arch, and (3) its encircling band is closed and nonadjustable, where as described below the strap is open and adjustable to ensure proper fit, compressive support to the arch and comfort.

What is needed is a device which is more comfortable, simpler, easier to apply, cost-effective, yet still counters the forces of pronation and heel spur syndrome. The present invention satisfies the need for further improvements in this area.

BRIEF SUMMARY OF THE INVENTION

The present invention provides a new and simplified apparatus for supporting the longitudinal arch which stabilizes the foot against the forces of pronation with increased comfort to the wearer. The key element in this invention is the specially designed, strategically placed, rubberized, resilient pad. The convex side of this pad presses up against the longitudinal arch, opposes its collapse, and thus resists and limits the forces of pronation. The pad, contained within the strap, is further aided in stabilizing the longitudinal arch by the pressure of the circumferential wrapping around the arch by the strap itself.

Reducing pronation will accomplish two main goals. (1) There will be less foot fatigue because fewer muscles will have to be used to stabilize the foot, and (2) heel pain from heel spur syndrome will be alleviated because reduced pronation will lessen the tension on the plantar fascia. In other words, use of this device should greatly diminish foot problems associated with excessive pronation. In comparison to the other apparatuses/devices previously described, this invention affords the following advantages: (1) Increased comfort to wearer and better shoe fit because of the slim nature of the device; (2) Less potential skin irritation because the device contains no stitching and there are no exposed VELCRO fastener straps; (3) Simpler self-application because of the design concept; (4) Simplicity of choice because one size (of each model) fits all, both right and left; (5) Less expensive to manufacture because of simplicity of design and lack of stitching; (6) Can be used by physicians as a temporary device in lieu of taping and strapping; (7) Over-the-counter availability will enhance early self-treatment which may avoid costly medical treatment; and (8) Can be utilized on a wide scale by persons in occupations requiring more than usual standing or walking.

In particular the invention is a device for stabilizing a foot and limiting pronation and heel spur syndrome. The foot has a longitudinal arch and a dorsal or top surface opposing the arch. The device comprises a flexible, substantially nonextensible, elongated, foam-covered laminate for encircling the longitudinal arch to in part stabilize it. The laminate tapers away from that portion fixed to the pad so that when it is applied to the foot the tapered portion extends across the top of the foot opposite the arch and is less obtrusive.

A substantially elastic elastomeric pad, which regains substantially all of its original thickness after repeated compressions, is fixed to the laminate for absorbing energy and defending against shock. The laminate and pad when applied to the foot disposes the pad at a predetermined position under the longitudinal arch to minimize the effects of pronation. The pad has a convex surface. The convex surface extends outwardly from the laminate so that the convex surface extends into the arch at the predetermined position.

A hook-type fastener, having a hook portion fixed to one end of the laminate with the an eye portion being the exterior surface of the laminate, secures the laminate and pad to the foot at the predetermined position, yet allows for variations in size.

The fastener and pad are fixed to the laminate without stitching so that comfort and thinness is enhanced.

The laminate and the fastener each have a predetermined length to allow a range of fastening positions of ends of the laminate to each other. The length of the laminate and the fastener being chosen to accommodate all possible sizes of the foot.

The laminate, pad and fastener have a longitudinal axis and wherein the laminate, pad and fastener are symmetric about the longitudinal axis so that the device is equally applicable to a left and right foot in the same manner.

These advantages and other aspects of this invention will be apparent from the detailed description and drawings which follow wherein like elements are referenced by like numerals.

BRIEF DESCRIPTION OF THE DRAWINGS

FIG. 2 is an outside plan view of the device showing additional general dimensions. The top portion of the Velcro-type fastener above the dotted line indicates that portion which is adhesively or otherwise bonded to the exterior surface of the device in a non-stitched fashion. The dotted line indicates the underlying narrow end of the device itself.

FIG. 3 is a cross-sectional view of the device showing the various layers which make up the device (not necessarily to scale).

FIG. 4 is an inside plan view of the device indicating its general shape and proportions, with the shaded portion of the VELCRO fastener indicating the hook portion and the dotted outline indicating the pad placement between the two foam layers.

FIG. 5a is top plan view of just the rubberized pad in the device.

FIG. 5b is cross-sectional view of just the rubberized pad in the device.

The invention and its various embodiments may now be understood by turning to the following detailed description.

DETAILED DESCRIPTION OF THE PREFERRED EMBODIMENTS

Figure 1:
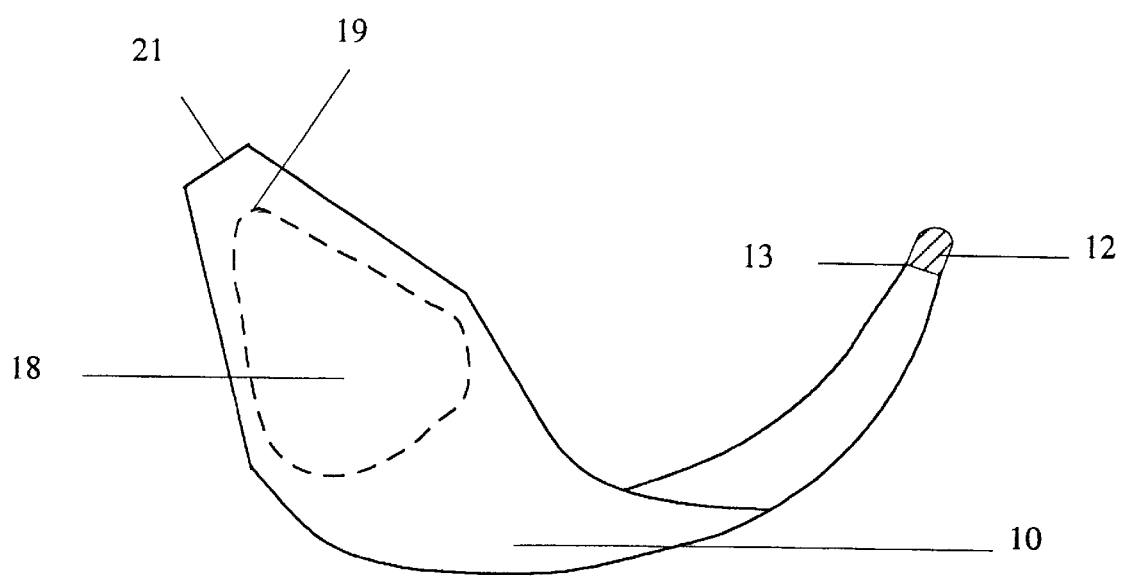
FIG. 1 is a perspective view of the device in an open and slightly curved configuration to show its general dimensions. The shaded portion of the Velcro-type fastener indicates that this portion contains the hooks which fasten to the exterior surface of the strap when applied. The dotted outline indicates the pad placement. Throughout the specification, "exterior" or "outside" is meant to refer to that portion of the device which is exposed or on the outside of or not touching the foot after the device is applied to the foot as intended. "Interior" or "inside" is meant to refer to that portion of the device which is not exposed or on the inside of or touching the foot after the device is applied to the foot as intended.

A supportive device for the longitudinal arch of the foot is comprised of a fabric-coated elasticized strap enclosing a specially designed pad of rubberized material. This strap is wrapped snugly around the longitudinal arch with the enclosed pad strategically placed to provide optimum arch support and secured by a VELCRO fastener strip. A tapered strap of fabric coated foam material (general dimensions 11" by 3"), is provided with a specially designed, triangular-shaped, rubberized pad (general dimensions 3" by 2.5" and 3/16" thickness). The narrow end of the pad points toward the wider end of the strap. The flat side of the pad is bonded to the inside of the device at the wider end and covered with a thin foam material. The convex side of the pad is in contact with the foot when the device is applied. A VELCRO fastener (general dimensions 2" by 1") secures the device to the foot. FIG. 1 shows only one half of the Velcro-type fastener (shaded area) 12, which is the portion which when pressed into the exterior surface of laminate body 10, fastens the device to the foot, which exterior surface acts as the eye portion of the fastener.

FIG. 1 shows in perspective view a flexible tapered strip of fabric-coated foam material body 10 having in the illustrated embodiment general dimensions 11" by 3", with a specially designed, triangular-shaped, rubberized resilient pad 18, which again in the illustrated embodiment measures about 3" in the longitudinal direction of device by 2.5" in an orthogonal direction and ³⁄₁₆" in thickness. Pad 18's outer outline is curvilinear and is chosen to comfortably conform to the cavity of the arch. The narrow end of the pad 19 points toward the wider end 21 of the device. The flat side of pad 18 is bonded to the inside of the device at the wider end 21 and covered with a thin foam material. The convex side 23 of the pad 18 as shown in FIG. 3 is in contact with the foot when the device is applied as intended. A plastic VELCRO fastener 12, which in the illustrated embodiment has dimensions 2" by 1", is adhesively fixed, heat bonded, or imbedded in the narrow end 13 of the strip to secure it. Fastener 12 may by fixed to the exterior, or interior surface of body 10, or have a thin split attaching portion which sandwiches body 10 and is fixed to both its interior and exterior surfaces. Exterior attachment is shown in FIG. 3 only as an illustration.

FIG. 2 shows a outside plan view of the device wherein surface of body 10 has a nappy or felt-like surface texture to function as the eye portion of the Velcro fastener and is provided near narrow end 13 with a VELCRO fastener.

FIG. 3 is a cross-sectional view taken through lines 3—3 of FIG. 2 and illustrates that the VELCRO fastener is adhesively fixed to the device at or near narrow end 13 with a portion of the VELCRO fastener 12 overlapping a portion of the adjacent outside surface of body 10. Pad 18 is securely fixed or captured with a pocket at the opposing end 21 beneath a pocket covering 16. Covering 16 is adhesively secured to the interior surface of body 10, and is fully surrounded by covering material as best depicted in the inside view of the device as shown in FIG. 4.

Pad 18 is shown in isolation of the other elements of the device in FIG. 5a in plan view and in side elevational view in FIG. 5b. Other shapes and proportions may be utilized other than those suggested by the illustrations without departing from the scope of the invention.

There are two embodiments, the Dress/Regular model and the Sports/Heavy Duty model, but one size fits all. The only difference between these embodiments is the thickness of the strap material. The Dress/Regular model uses a thinner material and the Sports/Heavy Duty model uses a heavier material.

Figure 6:
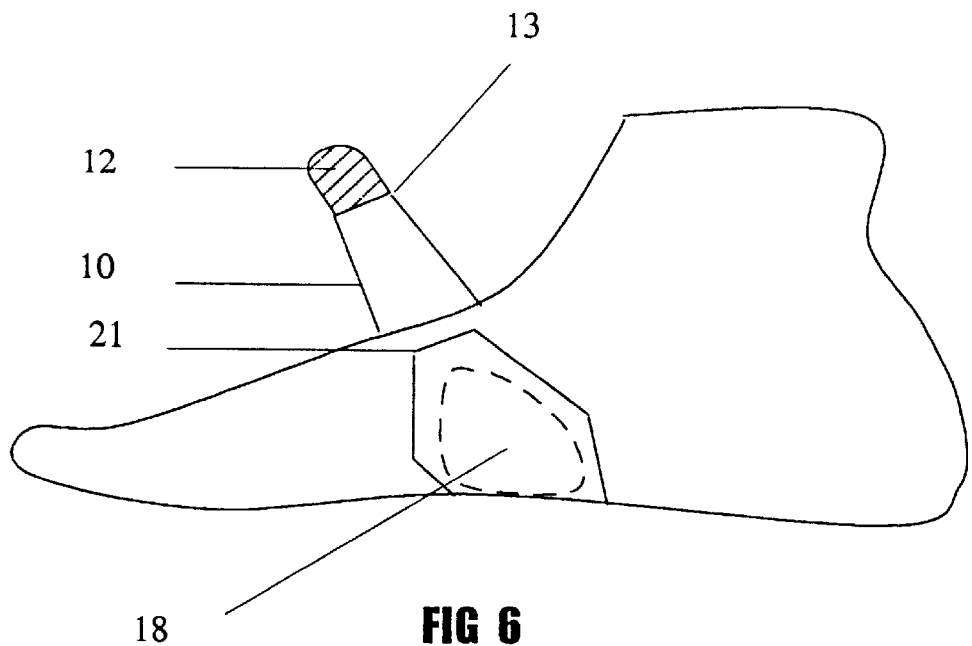
FIG. 6 is a medial (inside) view of the foot showing the placement of the pad end of the device and showing the other end just prior to snugly overlapping and securing.
Figure 7:
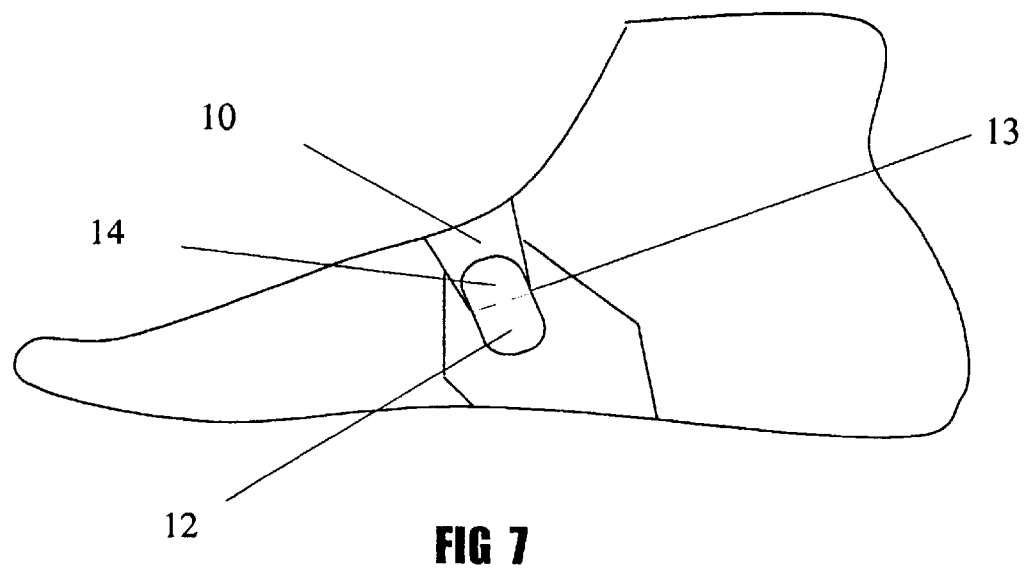
FIG. 7 is also a medial (inside) view of the foot with the device in its final, secured position.

The structure of the device now having been described, consider how it is applied to or wrapped around the foot. While placing and holding end 21 of the device under the arch side of the foot with one hand, end 13 is brought over the top of the foot with the other hand as shown in FIG. 6. After sufficient pressure is applied to ensure a snug fit with the arch, the hook side of the VELCRO fastener 12 on the strap end 13 is pressed into the exterior surface of body 10 of the device to secure it to the foot as shown in FIG. 7. Thus the only material in contact with the skin is the smooth interior surface of the device.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition structure, material or acts beyond the scope of the commonly defined meanings. The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. A device for stabilizing either a left or right foot and limiting pronation and heel spur syndrome, the foot having a longitudinal arch with a plantar aspect having medial and lateral regions defined by the longitudinal axis of the foot, comprising:

a flexible strap of an elastic material having first and second ends for wrapping around the foot;

a fastener for temporarily securing ends of said strap together on the foot; and an elastomeric pad formed of a material that substantially regains its original thickness after compression and has an edge surface and inwardly tapered sides extending from said edge surface generally in the direction of a longitudinal axis of the pad toward a narrow end of the pad, said pad being fixed to an inner surface of said strap for absorbing energy and defending against shock, at a position on said strap in proximity to the first end of said strap and oriented with the narrow end of said pad facing said first end of the strap such that when said strap and pad are applied to the foot, and said pad is disposed under said longitudinal arch exclusively outside the lateral region of the plantar portion of the longitudinal arch, the longitudinal axis of said pad is approximately perpendicular to the longitudinal axis of the foot, and said tapered portion of said pad is disposed from the longitudinal axis of the foot toward the medial region of the longitudinal arch to minimize effects of pronation.

2. The device of claim 1 wherein said strap is a foam covered laminate thus having a nonslip surface.

3. The device of claim 1 wherein said strap and said fastener have a longitudinal axis and wherein said strap and said fastener are symmetric about said longitudinal axis of said strap fastener, and, when the device is worn, said pad is asymmetrical about said longitudinal axis of said foot so that said device is equally applicable to a left and right foot in the same manner when said device is rotated 180 degrees about an axis perpendicular to said longitudinal axis of said device.

4. A device as in claim 1, wherein the entirety of said strap is made of a flexible material.

5. A device as in claim 4, wherein said strap is formed of a coated foam material.

6. A device as in claim 1, wherein said taper is monotonic.

7. A device as in claim 1, wherein said strap is of maximum width nearer the first end than the second end of the strap and tapers toward said first and second ends, and said pad is located on said strap at a region of said maximum width.

8. A device as in claim 1, wherein said strap and pad have lateral symmetry about the longitudinal axis of the strap.

9. A method of treating a foot by limiting pronation and heel spur syndrome, the foot having a longitudinal arch with a plantar aspect having medial and lateral regions defined by the longitudinal axis of the foot, comprising wrapping the foot with an elastic strap, the strap bearing an elastomeric pad formed of a material that substantially regains its original thickness after compression and has an edge surface and inwardly tapered sides extending from said edge surface generally in the direction of a longitudinal axis of the pad toward a narrow end of the pad, said pad being fixed to an inner surface of said strap for absorbing energy and defending against shock; and positioning on said strap on the foot such that said pad is disposed under said longitudinal arch exclusively outside the lateral region of the plantar portion of the longitudinal arch, the longitudinal axis of said pad is approximately perpendicular to the longitudinal axis of the foot, and said tapered portion of said pad is disposed from the longitudinal axis of the foot toward the medial region of the longitudinal arch to minimize effects of pronation.

\* \* \* \* \*